Jan. 19, 1943. G. W. WEAVER Plant Pat. 565

ROSE

Filed July 20, 1942

Inventor
G. W. Weaver
By Annar Lee Weaver
Administratrix of the Estate
of George Washington Weaver, deceased.
By Robb & Robb
Attorneys Patented Jan. 19, 1943

Plant Pat. 565

UNITED STATES PATENT OFFICE

565

ROSE

George Washington Weaver, deceased, late of Ontario, Calif., by Annar Lee Weaver, administratrix, Ontario, Calif., assignor to Armstrong Nurseries, Inc., Ontario, Calif., a corporation of California Application July 20, 1942, Serial No. 451,625

1 Claim. (Cl. 47—61)

The present discovery relates to a new and distinct variety of hybrid tea rose plant, originating as a sport found on a bush plant of the well-known "Texas Centennial" rose.

The dominating characteristics of this new rose are its strong and vigorous climbing form and habit of producing many more flowers in the spring than can be found at any one time on the bush parent, and having no apparent tendency to revert to bush form when propagated vegetatably by budding, as sometimes occurs in these climbing sports of bush plants.

As regards its other characteristics, particularly in color and form of the flower, no differences are notable.

Figure 1:
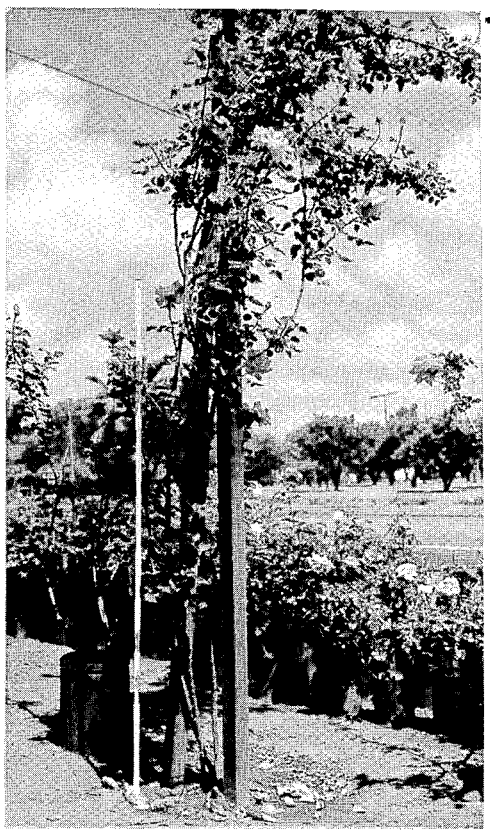
Figure 2:
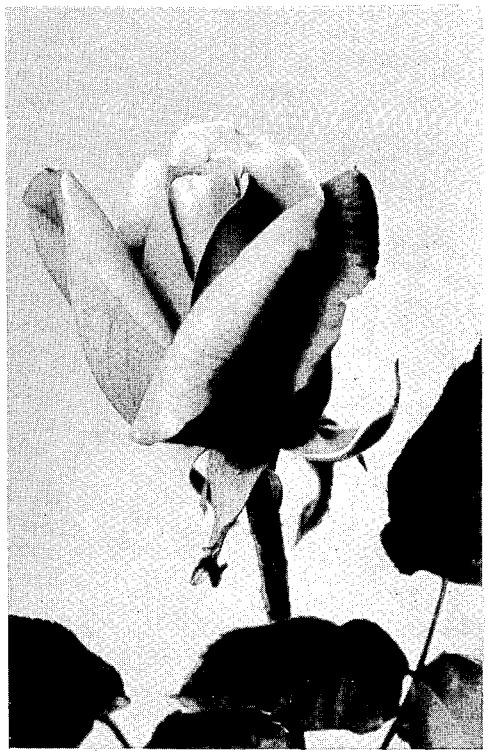

In the accompanying illustration:

Figure 1 is an elevational view showing the climbing characteristic of the new plant in comparison with a six-foot rule, and Figure 2 is a detailed view of a single flower partially open and adjacent foliage.

The following is a detailed description of the plant and flower of this new variety of rose plant, all color terminology being in accord with Ridgway's Color Standard:

Type: Hardy; climbing; outdoor.

Class: Climbing hybrid tea.

Discovery: By George W. Weaver, of Ontario, California.

Breeding: Sport.

*Parent.*—"Texas Centennial."

Propagation: The distinguishing characteristics have been found to come true to form by the following method of reproduction which is the only one tried: by budding.

*Flower*

Locality where grown: Ontario, California.

Flowers borne: Singly and often several to stem in irregular cluster; on strong, long stems.

Quantity of bloom: Abundant; outdoors.

Continuity: One season to intermittent.

Fragrance: Moderate; combination of tea and spicy.

Bud:

*Pedicel.*—Long; heavy; erect; rough; few gland-tipped cilia; prickles. *Color*—near Mignonette Green, Plate XXXI, with a tinge of Red, near Ox-blood Red, Plate I. The prickles are also an Ox-blood Red color.

*Before calyx breaks.*—*Size*—medium to large. *Form*—short, pointed, with a conspicuous neck; with gland-tipped cilia on the surface of the bud; with stout, entire connivent sepals extending beyond the tip of the bud equal to about ¼ of its length. There are variations in the appendages of the sepals. Many buds have long foliaceous appendages.

*As calyx breaks.*—*Color*—between Garnet Brown, Plate I, and Nopal Red, Plate I. Inner surface of sepal—with fine, woolly tomentum. The margins of two sepals are lined with fine woolly tomentum, two other sepals are lined with stipitate glands. The fifth sepal has one margin lined with woolly tomentum and the other margin lined with stipitate glands.

*As first petal opens.*—*Size*—medium to large. *Form*—globular. Color—outside; between Spinel Red, Plate XXVI, and Rose Red, Plate XII, with a slight tinge of Pinard Yellow, Plate IV, at the point of attachment. The outside surface of the first petals seems to have faded splotches on them; inside—near Rose Red, Plate XII, and shades into near Light Cadmium, Plate IV, at place of attachment. Opening—opens up well. It is retarded by severe hot weather.

Bloom:

*Size, when fully open.*—Large; from five inches to six inches across.

*Petalage.*—Double (more petals, but the stamens not hidden). When the flower is fully open, all the reproductive organs are visible. From 20 to 30 petals, arranged regularly. Some of the outside petals are 2⅝ inches wide and the same in length.

*Form.*—High center; becoming very open high centered; petals remaining at first tightly cupped, rolled outward; becoming at maturity, very loosely cupped, rolled outward.

Petals: Thick; with inside slightly satiny and outside shiny.

*Shape.*—Outside—ovate. The margins of the outside petals are entire with the apex flat, but they are curled under and undulating. Intermediate—ovate, with apex flat. Inside—oval, with apex flat.

This description of a newly opened flower was made from a rose grown outdoors in the month of May, 1942, at Ontario, California:

*Color.*—Outside petal, outside surface—between Deep Rose Pink, Plate XII, and Spinel Pink, Plate XXVI. The veins are easily seen and slightly of a darker hue. The petal is slightly wrinkled near the place of attachment. There is also a spot of Yellow (near Light Cadmium, Plate IV) at the place of attachment; inside surface—same as outside surface but nearer Spinel Pink, Plate XXVI, being darker near the apex and fading slightly. There is a splotch of Yellow (near Pinard Yellow, Plate IV) at the place of attachment. Intermediate petal, outside surface—between Thulite Pink, Plate XXVI, and Deep Rose Pink, Plate XII, becoming slightly wrinkled near the place of attachment. Place of attachment is near Mustard Yellow, Plate XVI; inside surface—near Deep Rose Pink, Plate XII, and fading to near Safrano Pink, Plate II, at base of petal. Naples Yellow, Plate XVI, at place of attachment. Inner petal, outside surface—between Deep Rose Pink, Plate XII, and Thulite Pink, Plate XXVI, nearer Thulite Pink. The outside surface of the petal is slightly tinted with Shrimp Pink, Plate I, near the base of the petal. It is also near Empire Yellow, Plate IV, at the place of attachment. The inside surface of the petal is tinted with Safrano Pink, Plate II, near the base of the petal and shades into a Maize Yellow, Plate IV, at point of attachment; inside surface—between Deep Rose Pink, Plate XII, and Thulite Pink, Plate XXVI, but slightly darker than the outside surface.

This description was made from a rose that was open for three days outdoors, in the month of May, 1942, at Ontario, California:

*Color.*—Outside petal, outside surface—near Spinel Pink, Plate XXVI, and shading into near Lemon Chrome, Plate IV, at the point of attachment; inside surface—near Rose Color, Plate XII, but a little deeper Red. At point of attachment the color shades into near Pinard Yellow, Plate IV. Inside petal, outside surface—near Spinel Pink, Plate XXVI, but slightly lighter in color than the outside petal. At point of attachment color is near Buff Yellow, Plate IV; inside surface—near Rose Color, Plate XII, and shading into near Buff Yellow, Plate IV, at point of attachment.

*General color effect.*—Newly opened flower—near Deep Rose Pink, Plate XII. Three days open—near Rose Color, Plate XII.

*Behavior.*—Drop off cleanly; fading brown; affected by hot weather. Severe heat turns the outside petals of the bud brown.

*Flower longevity.*—5 days in May.

*Reproductive organs*

Stamens: Very many; arranged regularly about pistils, tucked in calyx.

Filaments: Medium to long. They vary in color from Geranium Pink, Plate I, to Carmine, Plate I; most with anthers.

Anthers: Medium to large; all open at once; color, Near Amber Yellow, Plate XVI. The place of dehiscence is near Mars Yellow, Plate III.

Pollen: Moderate to abundant; color, between Mars Yellow, Plate III, and Orange, Plate III.

Pistils: Very many.

Styles: Even; medium to long; medium to heavy; very bunched; free, exerted and villous.

Stigma: The stigmatic surface is near Honey Yellow, Plate XXX, and sides of stigma are penciled with Carmine, Plate I.

Ovaries: Some protruding from calyx.

Hips: Rarely setting hips.

Sepals: Permanent; long; spear-shaped; recurved.

*Color.*—Inside—between Water Green, Plate XLI, and Pale Dull Green Yellow, Plate XVII, with thick overlay of white tomentum; Outside—between Courge Green, Plate XVII, and Parrot Green, Plate VI, with faint streak of Dull Green Yellow, Plate XVII, down center and near base of the sepal.

*Plant*

Foliage:

*Leaves.*—Compound of five leaflets; normally abundant. The compound leaf is from five to six inches long and from three to four inches wide. Medium to large; moderately thin, soft.

*Leaflets.*—Ovate with apex acute; base round; serrate.

*Color.*—Mature, upper surface—between Dark Yellow Green, Plate XXXII, and Dark Cress Green, Plate XXXI, the mid-rib being lighter, near Chrysolite Green, Plate XXXI; under surface—between Rainette Green and Light Cress Green, Plate XXXI. Young, upper surface—between Maroon, Plate I, and somewhat glossy Morocco Red, Plate I, shading into Olive Green, Plate IV, near apex; under surface—between Liver Brown, Plate XIV, and Claret Brown, Plate I, etched with Olive Green, Plate IV, near apex and on mid-rib at place of attachment.

*Rachis.*—Medium to heavy. Upper side—grooved; hairy; glandular. Under side—sparsely prickly.

*Stipules.*—Of medium length; moderately narrow; with long points turning out at an angle of more than 45°. Gland ciliate.

*Disease.*—Moderately subject to mildew.

Growth:

*Habit.*—Climbing; much branched.

*Growth.*—Vigorous.

*Canes.*—Medium to heavy

*Main stems.*—Color—between Yellowish Oil Green, Plate V, and Grape Green, Plate XLI. As the cane grows older the bark becomes somewhat woody and rough. *Large prickles*—Many; medium to long; hooked downward; with base medium. Color—near Avellaneous; Plate XL, and having a silver tint on the older canes. *Small prickles*—none. *Hairs*—none.

*Branches.*—Between Oil Green, Plate V, and Lettuce Green, Plate V. *Large prickles*—many; medium to long; hooked downward; with narrow to medium base. Color—near Sudan Brown, Plate III, and shiny. *Small prickles*—none. *Hairs*—none.

*New Shoots.*—Between Absinthe Green, Plate XXXI, and Lettuce Green, Plate V, with a reddish hue on one of side stems and at base of some of the prickles. *Large prickles*—many; medium length; hooked downward; with short, narrow base.

Color—near Javel Green, Plate V, and shading into a reddish hue near the base. *Small prickles*—none. *Hairs*—none.

What is claimed is:

A new and distinct variety of hybrid tea rose plant, characterized as to novelty by its strong and vigorous climbing habit and the habit of producing many more flowers in the spring than can be found at any one time on its bush parent, substantially as shown and described.

ANNAR LEE WEAVER,
*Administratrix of the Estate of George Washington Weaver, Deceased.*